(12) United States Patent
Beeckler et al.

(10) Patent No.: US 10,638,976 B2
(45) Date of Patent: May 5, 2020

(54) METHOD OF CONSTRUCTING IRRIGATED BALLOON CATHETER

(71) Applicant: BIOSENSE WEBSTER (ISRAEL) LTD., Yokneam (IL)

(72) Inventors: Christopher Thomas Beeckler, Brea, CA (US); Joseph Thomas Keyes, Glendora, CA (US); Assaf Govari, Haifa (IL)

(73) Assignee: BIOSENSE WEBSTER (ISRAEL) LTD, Yokneam (IL)

( * ) Notice: Subject to any disclaimer, the term of this patent is extended or adjusted under 35 U.S.C. 154(b) by 296 days.

(21) Appl. No.: 15/141,751

(22) Filed: Apr. 28, 2016

(65) Prior Publication Data

US 2017/0311893 A1 Nov. 2, 2017

(51) Int. Cl.
*B29C 65/16* (2006.01)
*A61B 5/00* (2006.01)
(Continued)

(52) U.S. Cl.
CPC ............ *A61B 5/6853* (2013.01); *A61B 5/042* (2013.01); *A61B 5/6857* (2013.01);
(Continued)

(58) Field of Classification Search
CPC ....... B29C 65/16; B29C 65/48; A61B 5/6853; A61B 5/042; A61B 5/6857; A61B 5/1492
See application file for complete search history.

(56) References Cited

U.S. PATENT DOCUMENTS

| | | | |
|---|---|---|---|
| 3,316,896 A | 5/1967 | Thomasset | |
| 4,587,975 A | 5/1986 | Salo et al. | |

(Continued)

FOREIGN PATENT DOCUMENTS

| | | |
|---|---|---|
| CN | 102271607 A | 12/2011 |
| CN | 203539434 U | 4/2014 |

(Continued)

OTHER PUBLICATIONS

U.S. Appl. No. 14/578,807, entitled Balloon for Ablation Around Pulmonary Vein, 14 pages.
(Continued)

*Primary Examiner* — Daniel McNally
(74) *Attorney, Agent, or Firm* — Etan S. Chatlynne; Roberts Calderon Safran & Cole P.C.

(57) ABSTRACT

A method of constructing an inflatable electrode assembly configured for irrigation, comprises: providing a flex circuit having a substrate with a pre-formed aperture, the substrate constructed of a material having a greater heat resistance or a first melting temperature; providing a balloon member with a membrane, the membrane constructed of a material having a lesser heat resistance or a second melting temperature lower than the first melting temperature of the substrate; affixing the substrate to the membrane wherein a surrounding portion of the substrate around the pre-formed aperture masks a surrounding portion of the membrane so as to expose a target portion of the membrane; and applying heat to the target portion of the membrane through the pre-formed aperture of the substrate, wherein the heat applied, without melting the substrate, melts the target portion of the membrane in forming an aperture in the membrane.

22 Claims, 8 Drawing Sheets

(51) Int. Cl.
*A61B 5/042* (2006.01)
*A61B 18/14* (2006.01)
*B29C 65/48* (2006.01)
*A61B 18/00* (2006.01)
*A61B 17/00* (2006.01)
*A61M 25/10* (2013.01)
*B29L 31/00* (2006.01)

(52) U.S. Cl.
CPC .......... *A61B 18/1492* (2013.01); *B29C 65/16* (2013.01); *B29C 65/48* (2013.01); *A61B 2017/00526* (2013.01); *A61B 2018/0016* (2013.01); *A61B 2018/0022* (2013.01); *A61B 2018/00029* (2013.01); *A61B 2018/00083* (2013.01); *A61B 2018/00357* (2013.01); *A61B 2018/00375* (2013.01); *A61B 2018/00577* (2013.01); *A61B 2018/00642* (2013.01); *A61B 2018/00702* (2013.01); *A61B 2018/00791* (2013.01); *A61B 2018/00821* (2013.01); *A61B 2018/1405* (2013.01); *A61B 2018/1407* (2013.01); *A61B 2018/1465* (2013.01); *A61B 2018/1497* (2013.01); *A61B 2218/002* (2013.01); *A61B 2562/125* (2013.01); *A61M 2025/1086* (2013.01); *B29L 2031/7542* (2013.01)

(56) References Cited

U.S. PATENT DOCUMENTS

| | | | |
|---|---|---|---|
| 4,805,621 | A | 2/1989 | Heinze et al. |
| 5,178,957 | A * | 1/1993 | Kolpe ................ A61N 1/04 428/458 |
| 5,584,830 | A | 12/1996 | Ladd et al. |
| 5,702,386 | A | 12/1997 | Stern et al. |
| 5,797,903 | A | 8/1998 | Swanson et al. |
| 5,971,983 | A | 10/1999 | Lesh |
| 6,012,457 | A | 1/2000 | Lesh |
| 6,024,740 | A | 2/2000 | Lesh et al. |
| 6,042,580 | A | 3/2000 | Simpson |
| 6,123,718 | A | 9/2000 | Tu et al. |
| 6,164,283 | A | 12/2000 | Lesh |
| 6,176,832 | B1 | 1/2001 | Habu et al. |
| 6,226,542 | B1 | 5/2001 | Reisfeld |
| 6,301,496 | B1 | 10/2001 | Reisfeld |
| 6,471,693 | B1 | 10/2002 | Carroll et al. |
| 6,522,930 | B1 | 2/2003 | Schaer et al. |
| 6,814,733 | B2 | 11/2004 | Schwartz et al. |
| 6,892,091 | B1 | 5/2005 | Ben-Haim et al. |
| 6,986,744 | B1 | 1/2006 | Krivitski |
| 6,997,924 | B2 | 2/2006 | Schwartz et al. |
| 7,156,816 | B2 | 1/2007 | Schwartz et al. |
| 7,340,307 | B2 | 3/2008 | Maguire et al. |
| 7,442,190 | B2 | 10/2008 | Abbound et al. |
| 7,536,218 | B2 | 5/2009 | Govari et al. |
| 7,756,576 | B2 | 7/2010 | Levin |
| 7,842,031 | B2 | 11/2010 | Abboud et al. |
| 8,357,152 | B2 | 1/2013 | Govari et al. |
| 9,126,023 | B1 * | 9/2015 | Sahatjian ............... A61M 25/10 |
| 9,289,141 | B2 | 3/2016 | Lowery et al. |
| 2001/0031961 | A1 | 10/2001 | Hooven |
| 2002/0002369 | A1 | 1/2002 | Hood |
| 2002/0077627 | A1 | 6/2002 | Johnson et al. |
| 2003/0050637 | A1 | 3/2003 | Maguire et al. |
| 2003/0060820 | A1 | 3/2003 | Maguire et al. |
| 2005/0070887 | A1 | 3/2005 | Taimisto et al. |
| 2006/0013595 | A1 | 1/2006 | Trezza et al. |
| 2006/0135953 | A1 | 6/2006 | Kania et al. |
| 2007/0071792 | A1 * | 3/2007 | Varner ................ A61K 9/0024 424/427 |
| 2007/0287994 | A1 | 12/2007 | Patel |
| 2008/0018891 | A1 | 1/2008 | Hell et al. |
| 2008/0188912 | A1 * | 8/2008 | Stone ................ A61B 18/1492 607/99 |
| 2008/0249463 | A1 | 10/2008 | Pappone et al. |
| 2009/0182318 | A1 | 7/2009 | Abboud et al. |
| 2010/0324552 | A1 | 12/2010 | Kauphusman et al. |
| 2011/0130648 | A1 | 6/2011 | Beeckler et al. |
| 2011/0295248 | A1 | 12/2011 | Wallace et al. |
| 2012/0019107 | A1 | 1/2012 | Gabl et al. |
| 2012/0029511 | A1 | 2/2012 | Smith et al. |
| 2012/0071870 | A1 | 3/2012 | Salahieh et al. |
| 2012/0101413 | A1 | 4/2012 | Beetel et al. |
| 2012/0143177 | A1 | 6/2012 | Avitall |
| 2012/0191079 | A1 | 7/2012 | Moll et al. |
| 2013/0109982 | A1 | 5/2013 | Sato et al. |
| 2013/0165916 | A1 | 6/2013 | Mathur et al. |
| 2013/0165941 | A1 | 6/2013 | Murphy |
| 2013/0261692 | A1 | 10/2013 | Cardinal et al. |
| 2013/0282084 | A1 | 10/2013 | Mathur et al. |
| 2014/0018788 | A1 | 1/2014 | Engelman et al. |
| 2014/0058197 | A1 | 2/2014 | Salahieh et al. |
| 2014/0121470 | A1 | 5/2014 | Scharf et al. |
| 2014/0148805 | A1 | 5/2014 | Stewart et al. |
| 2014/0243821 | A1 * | 8/2014 | Salahieh ............... A61N 1/05 606/41 |
| 2014/0276756 | A1 | 9/2014 | Hill |
| 2014/0276811 | A1 | 9/2014 | Koblish et al. |
| 2014/0288546 | A1 | 9/2014 | Sherman et al. |
| 2014/0357956 | A1 | 12/2014 | Salahieh et al. |
| 2015/0025532 | A1 | 1/2015 | Hanson et al. |
| 2015/0157382 | A1 | 6/2015 | Avitall et al. |
| 2016/0175041 | A1 | 6/2016 | Govari et al. |
| 2016/0183877 | A1 | 6/2016 | Williams et al. |
| 2017/0042614 | A1 | 2/2017 | Salahieh et al. |
| 2017/0311829 | A1 | 11/2017 | Beeckler et al. |
| 2017/0312022 | A1 | 11/2017 | Beeckler et al. |
| 2017/0347896 | A1 | 12/2017 | Keyes et al. |
| 2018/0161093 | A1 | 6/2018 | Basu et al. |

FOREIGN PATENT DOCUMENTS

| | | |
|---|---|---|
| EP | 0779059 A1 | 6/1997 |
| JP | 11-076233 A | 3/1999 |
| JP | 2005-052424 A | 3/2005 |
| JP | 2012-024156 A | 2/2012 |
| WO | 0056237 A2 | 9/2000 |
| WO | 02/102231 A2 | 12/2002 |
| WO | 2008049087 A1 | 4/2008 |
| WO | 2011143468 A2 | 11/2011 |
| WO | 2013049601 A2 | 4/2013 |
| WO | 2013052919 A2 | 4/2013 |
| WO | 2013154776 A2 | 10/2013 |
| WO | 2015049784 A1 | 4/2015 |
| WO | 2015200518 A1 | 12/2015 |
| WO | 2016183337 A2 | 11/2016 |

OTHER PUBLICATIONS

Extended European Search Report for Application No. EP17165513.4 dated Sep. 18, 2017, 11 pages.
Extended European Search Report for Application No. EP17168393.1 dated Dec. 15, 2017, 12 pages.
Extended European Search Report for European Application No. 17201434.2, dated Feb. 1, 2019, 9 pages.
Extended European Search Report for European Application No. EP15201723, dated May 11, 2016, 7 pages.
Extended European Search Report for European Application No. EP17168518, dated Sep. 20, 2017, 9 pages.
Extended European Search Report for European Application No. EP17173893, dated Nov. 6, 2017, 8 pages.
Extended European Search Report for European Application No. EP17205876, dated Jun. 1, 2018, 13 pages.
Partial European Search Report for Application No. EP17168393.1 dated Sep. 13, 2017, 13 pages.
Partial European Search Report for European Application No. EP17205876, dated Feb. 22, 2018, 10 pages.

(56) References Cited

OTHER PUBLICATIONS

International Search Report and Written Opinion for Application No. PCT/IB2019/052313, dated Jul. 22, 2019, 8 pages.

* cited by examiner

METHOD OF CONSTRUCTING IRRIGATED BALLOON CATHETER

FIELD OF INVENTION

This invention relates to electrophysiologic (EP) catheters, in particular, EP catheters for mapping and/or ablation in the heart.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in various tissue regions in or near the heart, for example, the atria and/or and adjacent structures such as areas of the pulmonary veins, and left and right atrial appendages. Regardless of the sources, unwanted signals are conducted abnormally through heart tissue where they can initiate and/or maintain arrhythmia.

Procedures for treating arrhythmia include surgically disrupting the origin of the signals causing the arrhythmia, as well as disrupting the conducting pathways for such signals. More recently, it has been found that by mapping the electrical properties of the heart muscle in conjunction with the heart anatomy, and selectively ablating cardiac tissue by application of energy, it is possible to cease or modify the propagation of unwanted electrical signals from one portion of the heart to another. The ablation process destroys the unwanted electrical pathways by formation of non-conducting lesions.

A typical ablation procedure involves the insertion of a catheter having electrode(s) at its distal end into a heart chamber. An indifferent electrode is provided, generally adhered to the patient's skin. Radio frequency (RF) current is applied to the electrode(s), and flows between the surrounding media, i.e., blood and tissue and the indifferent electrode. The distribution of current depends on the amount of electrode surface in contact with the tissue, as compared to blood which has a higher conductivity than the tissue. Heating of the tissue occurs due to Joule heating. If the tissue is heated sufficiently, protein denaturation occurs; this in turn forms a lesion within the heart muscle which is electrically non-conductive.

A focal catheter works well, for example, when ablating a line of block in the atria. However, for tubular regions in or around the heart, this type of catheter is cumbersome, skill dependent, and time consuming. For example, when the line of block is to be made about a circumference of the tubular region, it is difficult to manipulate and control the distal end of a focal catheter so that it effectively ablates about the circumference. In current practice a line of block is accomplished by maneuvering the catheter from point to point and is highly dependent on the skill of the operator and can suffer from incomplete isolation of target areas such as the pulmonary vein ostia. However, done well, it can be very effective.

Catheters with circular ablation assemblies (or "lasso-type" catheters) are known. This type of catheter comprises a catheter body having at its distal end an ablation assembly with a preformed generally circular curve with an outer surface and being generally transverse to the axis of the catheter body. In this arrangement, the catheter has at least a portion of the outer circumference of the generally circular curve in contact with the inner circumference or ostium of a tubular region in or near the patient's heart, e.g., a pulmonary vein. However, one drawback with catheters of this type may be the relatively fixed size or circumference of the circular ablation assembly, which may not match the circumference of the tubular region undergoing treatment. Further, the variance in anatomy observed between subjects makes it difficult for a "one size fits all" approach.

Ablation catheters with inflatable assemblies or balloons are also known. Such balloons may include electrodes positioned on the outer surface of the balloons for ablating tissue and are typically inflated with a pressurized fluid source. More recently, inflatable catheter electrode assemblies have been constructed with flex circuits to provide the outer surface of the inflatable electrode assemblies with a multitude of very small electrodes. Examples of catheter balloon structures are described in U.S. application Ser. No. 14/578,807, titled Balloon for Ablation Around Pulmonary Vein, the entire content of which is incorporated herein by reference.

Flex circuits or flexible electronics involve a technology for assembling electronic circuits by mounting electronic devices on flexible plastic substrates, such as polyimide, Liquid Crystal Polymer (LCP), PEEK or transparent conductive polyester film (PET). Additionally, flex circuits can be screen printed silver circuits on polyester. Flexible printed circuits (FPC) are made with a photolithographic technology. An alternative way of making flexible foil circuits or flexible flat cables (FFCs) is laminating very thin (0.07 mm) copper strips in between two layers of PET. These PET layers, typically 0.05 mm thick, are coated with an adhesive which is thermosetting, and will be activated during the lamination process. Single-sided flexible circuits have a single conductor layer made of either a metal or conductive (metal filled) polymer on a flexible dielectric film. Component termination features are accessible only from one side. Holes may be formed in the base film to allow component leads to pass through for interconnection, normally by soldering.

However, where irrigation is desired or needed to cool and dilute the tissue region being ablated by an inflatable electrode assembly, perforation or the formation of irrigation apertures in a balloon membrane layer and an outer flex circuit substrate layer has posed numerous challenges. Where the apertures are formed in each layer separately, alignment of the apertures thereafter between the two layers has its difficulties. Where the apertures are formed in the two layers affixed to each other, methods for forming apertures in one layer may degrade or damage the other layer, especially where the two layers are constructed of material with different melting temperatures, such as Pellethane and polyimide. Patchworking the balloon structure with sections of perforated membrane and sections of perforated substrate can cause the balloon to misshapen, especially where the materials have different durometers.

Accordingly, a need exists for a method of constructing a catheter having an inflatable member or balloon with flex circuits and yet provides a plurality of irrigation apertures for irrigation of fluid from inside the balloon to outside. It is desirable that such method allows for the formation of irrigation apertures with uniformity and/or accuracy, without undesirable degradation or damage to the balloon membrane and flex circuit substrate, while enabling the balloon to maintain a desirable shape or configuration while inflated.

SUMMARY OF THE INVENTION

Embodiments of the present invention include a method of constructing an inflatable irrigated electrode assembly for an electrophysiology catheter. In some embodiments, the method comprises: providing a flex circuit having a substrate with a pre-formed aperture, the substrate constructed of a material with a greater heat resistance; providing an inflated balloon member with a flexible membrane, the membrane constructed of a material with a lesser heat resistance; affixing the substrate to the membrane with adhesive; the adhesive having a lower melting temperature than the flex circuit substrate, and applying heat through the pre-formed aperture of the substrate, the heat having a temperature sufficient to melt a portion of the membrane and the adhesive without degrading, damaging or melting the substrate, the portion of the membrane melted forming an aperture in the membrane.

In some embodiments, the substrate is constructed of a thermoset material or a material having a higher melting temperature relative to the lower melting temperature of the material from which the membrane is constructed, for example, polyimide.

In some embodiments, the membrane is constructed of thermoplastic polyurethane.

In some embodiments, the membrane is constructed of a flexible and elastic material.

In some embodiments, the heat applied reflows the portion of the membrane and the adhesive forming the aperture in the membrane.

In some embodiments, the applying heat includes inserting a soldering iron into the pre-formed aperture.

In some embodiments, the applying heat includes inserting a hot wire into the pre-formed aperture.

In some embodiments, the applying heat includes directing an energy beam from a laser into the pre-formed aperture to melt the target portion of the membrane.

In some embodiments, a method of constructing an inflatable electrode assembly configured for irrigation, comprises: providing a flex circuit having a substrate with a pre-formed aperture, the substrate constructed of a thermoset material or a material having a first melting temperature; providing a balloon member with a membrane, the membrane having a second melting temperature lower than the first melting temperature of the substrate; affixing the substrate to the membrane with an adhesive having a third melting temperature also lower than the first melting temperature, wherein a surrounding portion of the substrate around the pre-formed aperture masks a surrounding portion of the membrane and the adhesive so as to expose a target portion of the membrane; and applying heat to the target portion of the membrane through the pre-formed aperture of the substrate, wherein the heat applied, without degrading, damaging or melting the substrate, melts the target portion of the membrane and the adhesive in forming an aperture in the membrane.

In some embodiments, the heat applied creates a temperature between the first melting temperature of the membrane and the second and third melting temperatures of the substrate and the adhesive.

In some embodiments, the aperture in the membrane is larger than the pre-formed aperture in the substrate.

In some embodiments, affixing the substrate to the membrane includes applying an adhesive between the membrane and the surrounding portion of the substrate, wherein the heat applied through the aperture of the substrate reflows the membrane and the adhesive.

In some embodiments, a method of constructing an inflatable electrode assembly configured for irrigation, comprising: providing a flex circuit having a substrate with a pre-formed aperture, the substrate constructed of a thermoset material or a material having a higher melting temperature; providing an inflated balloon member with a flexible membrane, the membrane having a lower melting temperature; adhering the substrate to the membrane with adhesive, the adhesive also having a lower melting temperature than the substrate, wherein a first surrounding portion of the substrate around the pre-formed aperture frames an exposed target portion of the membrane and the adhesive while masking a second surrounding portion of membrane and the adhesive around the exposed target portion; and applying heat to the target portion of the membrane through the pre-formed aperture of the substrate, the heat creating a temperature sufficient to melt the target portion of membrane and the adhesive without melting or thermally damaging or degrading the first surrounding portion of the substrate.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
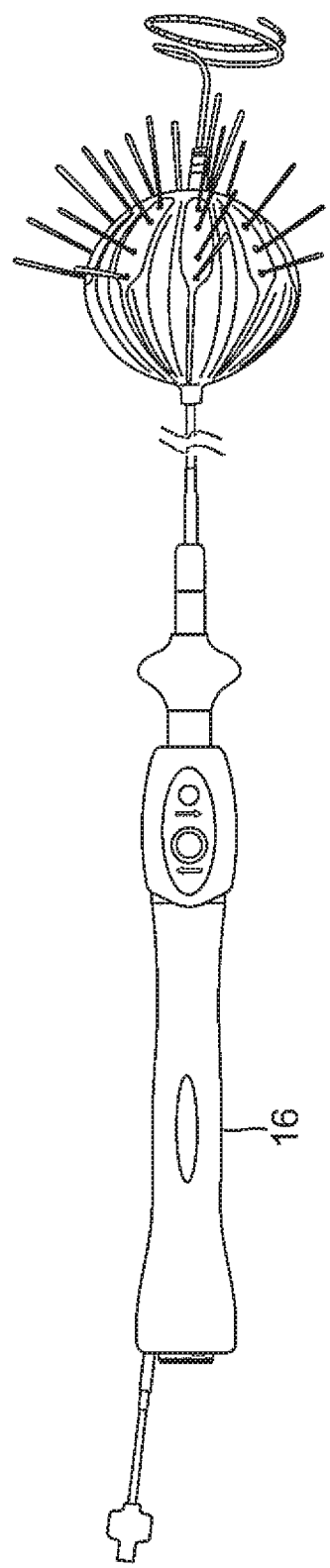
FIG. 1 is a top plan view of a catheter of the present invention, in accordance with an embodiment.
Figure 2A:
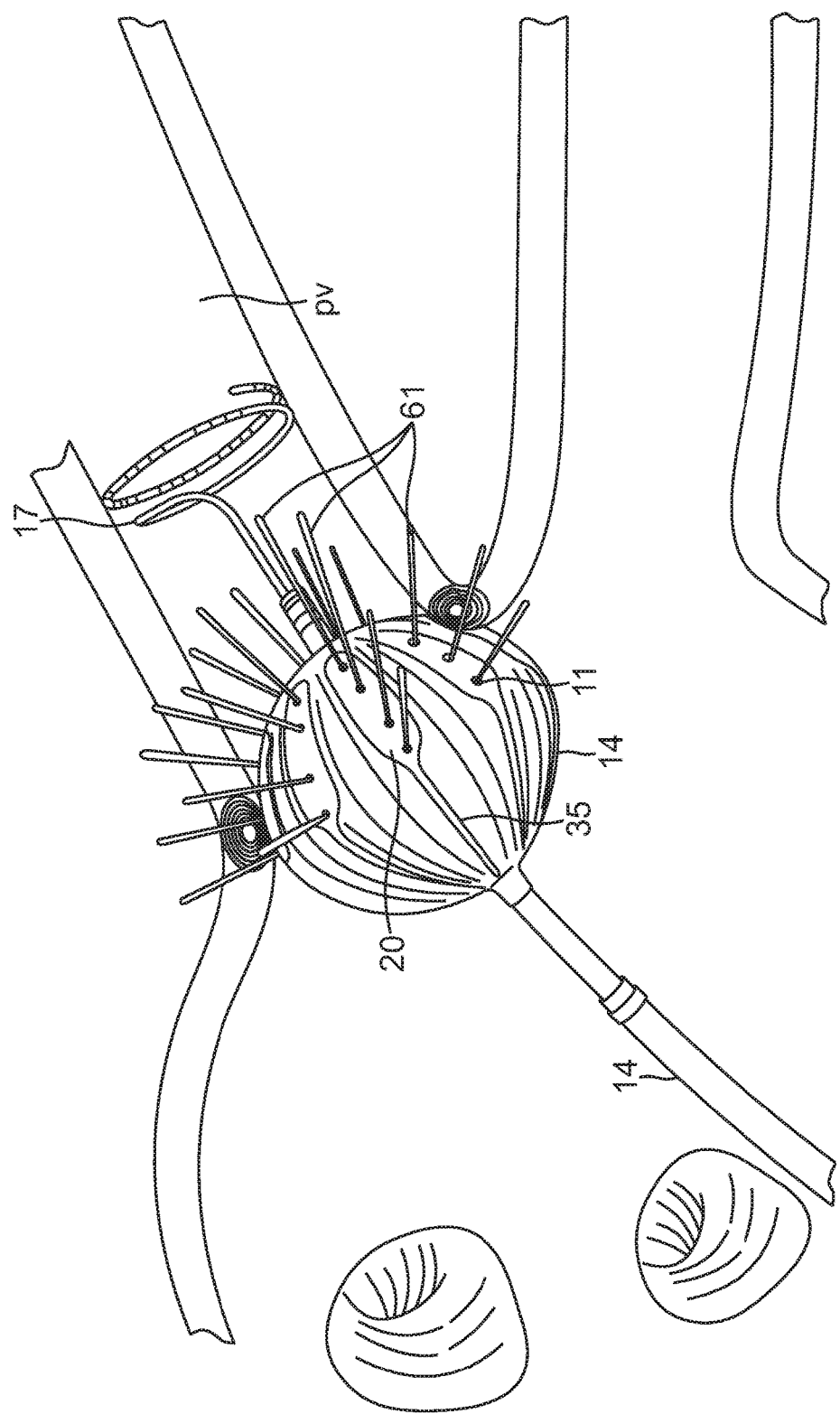
FIG. 2A is a side view of an inflatable electrode assembly deployed in the region of a pulmonary vein of the left atrium.

As shown in FIG. 1, the catheter 10 comprises an elongated catheter shaft 12, an inflatable electrode assembly 13 with a balloon member 14 having one or more flex circuits 15 on its outer surface, and a deflection control handle 16 attached to the proximal end of the catheter body 12. The catheter 10 may function in combination with a distal electrode assembly, for example, a lasso electrode assembly 17, for which the inflatable electrode assembly 13 can function as an anchor and/or stabilizer when the lasso electrode assembly 17 is in use, such as when inserted in a pulmonary vein PV of the left atrium, as shown in FIG. 2A.

Figure 3:
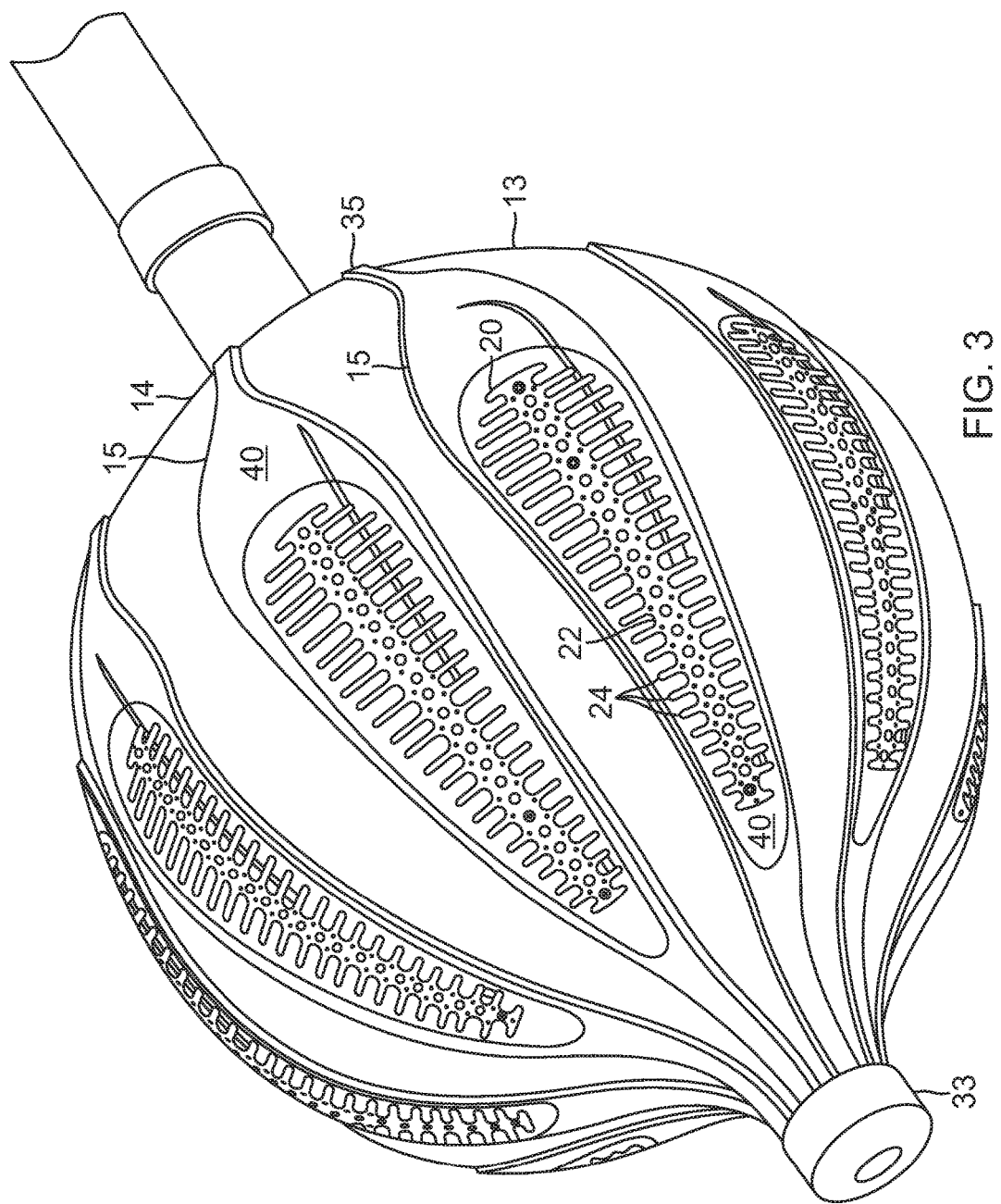
FIG. 3 is a detailed view of the inflatable electrode assembly in accordance with an embodiment of the present invention.

With reference to FIG. 3, each flex circuit on the balloon member 14 has an elongated electrode 20, configured with, for example, a longitudinal spine 22 and a plurality of fingers 24 that extend transversely from opposite sides of the spine. As show in FIG. 2A, the electrode 20 of each flex circuit 15 is configured for circumferential contact with tissue in a tubular region or ostium when the balloon member 14 is pressurized to expand the inflatable electrode assembly 13 by fluid from a remote fluid source (not shown). The fluid is delivered by an irrigation tubing 25 that extends from the control handle 16, along the length of the catheter body 12 and into an interior cavity of the balloon member 14. It is understood that the inflatable electrode assembly 13 assumes a collapsed configuration when entering a patient's vasculature and is expanded by inflation for deployment at a target site. In accordance with a feature of the present invention, the inflatable electrode assembly 13 is configured with a plurality of irrigation apertures 11 which advantageously allows fluid from inside the interior cavity of the balloon member 14 to pass to outside of the assembly 13 during deployment, for various purposes, including cooling surrounding tissue, improving lesion formation and minimizing the creation of char on or near the assembly 13. Although FIG. 2A illustrates the flow of fluid as stream jets 61, it is understood that the fluid may exit the irrigation apertures 11 at any desirable or appropriate rate, ranging between fluid seepage or weeping to stream jets.

Figure 4A:
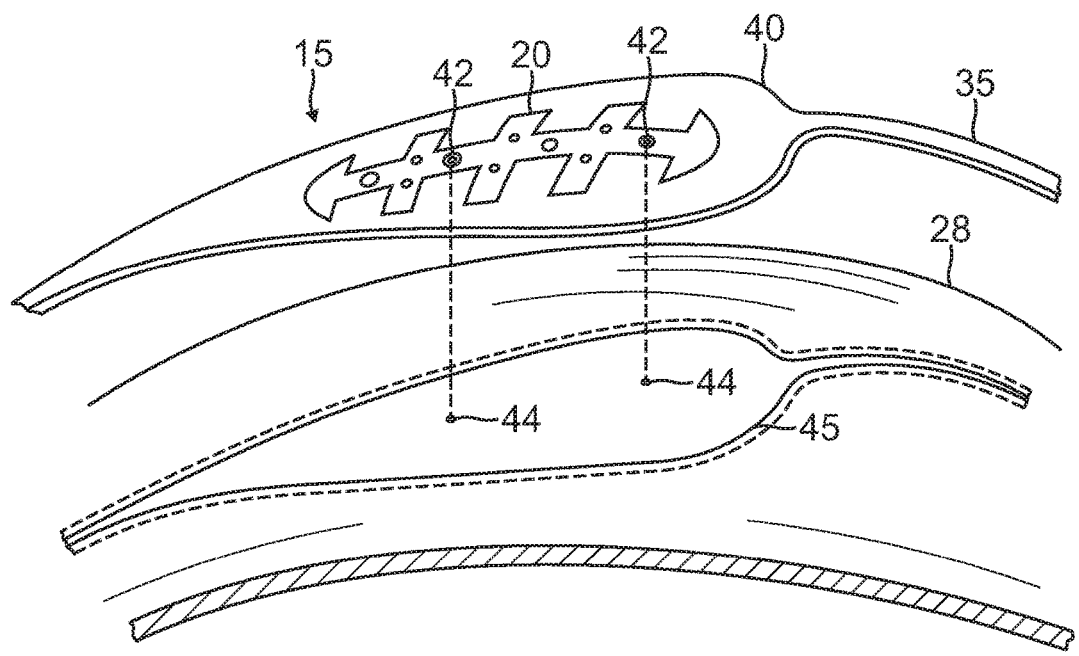
FIG. 4A is a side view of a flex circuit prior to affixation to a balloon membrane.

As shown in FIG. 4A, the balloon member 14 has a membrane 28 which is flexible and if appropriate or desired, also elastic. The membrane 28 is constructed of a thermoplastic material with a low durometer ranging between about 50 A and 55 D, and preferably between about 80 A and 50 D. A suitable material includes Pellethane, a medical-grade thermoplastic polyurethane elastomer, with superior resilience, low temperature properties and exceptionally smooth surfaces.

Figure 2B:
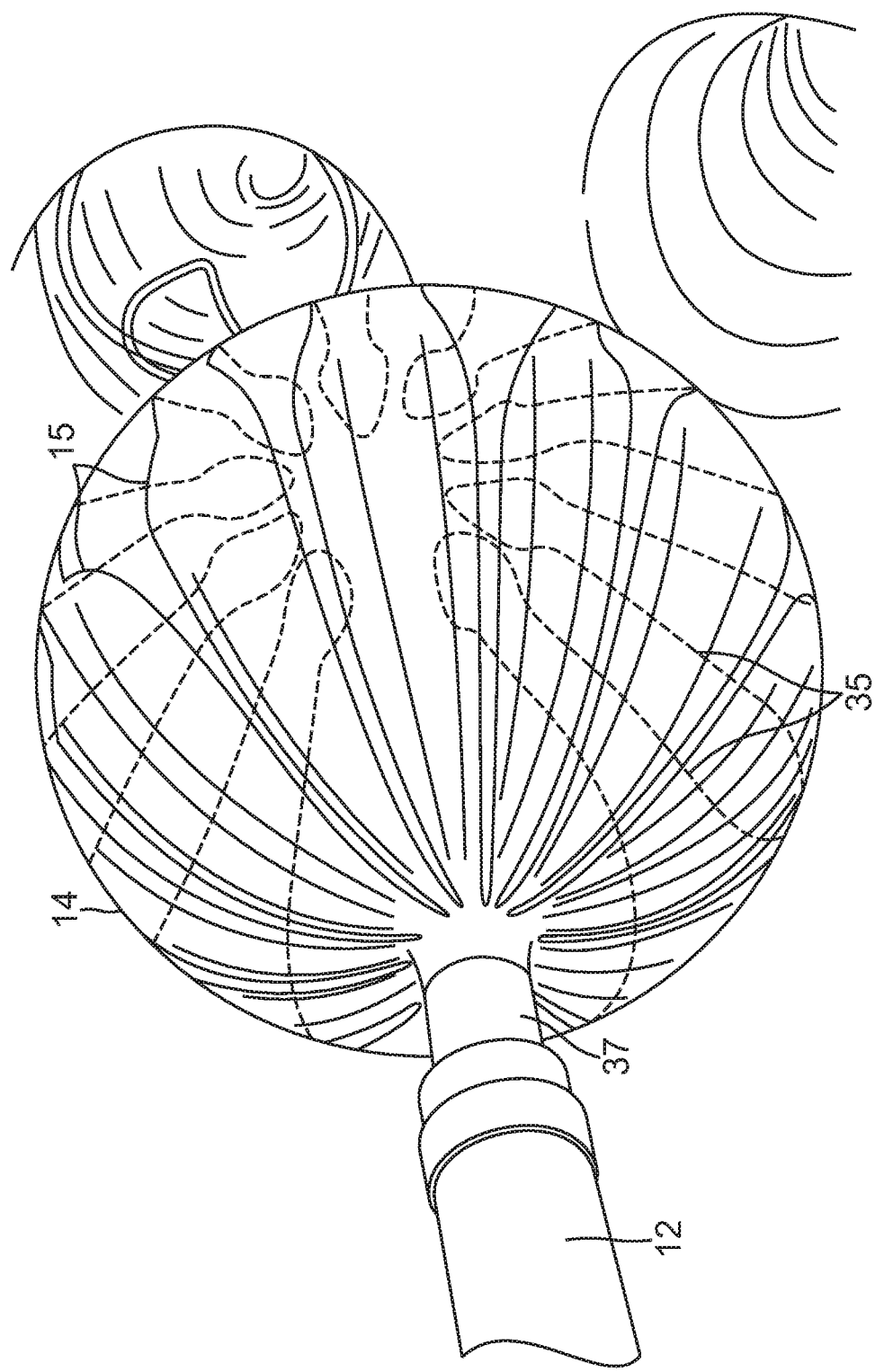
FIG. 2B is a perspective view of the inflatable electrode assembly in approach to a pulmonary vein of the left atrium.
Figure 5:
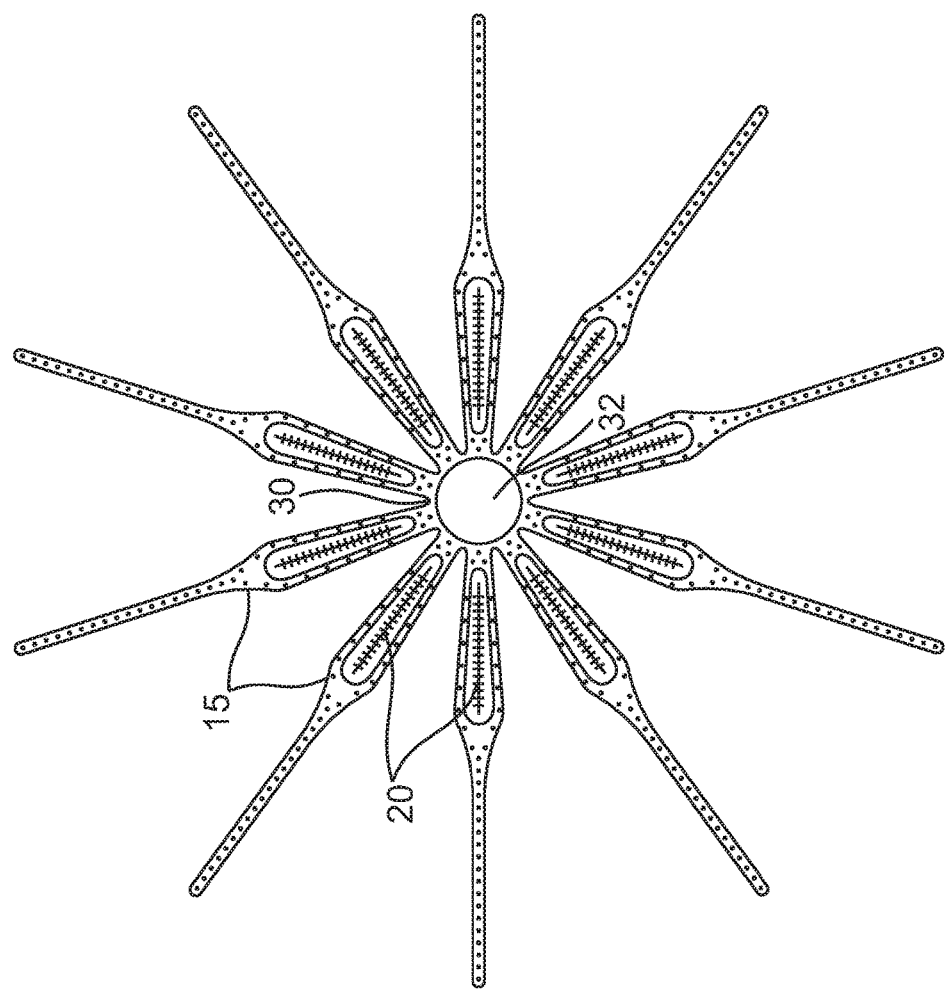
FIG. 5 is a top plan view of a flex circuit web, according to one embodiment.

Fixedly attached to an outer surface of the balloon membrane 28, for example, by an adhesive, are the plurality of flex circuits 15. As shown in FIG. 5, each flex circuit 15 may be connected at its distal end to the other flex circuits by a hub or circular portion 30 during manufacture, forming a flex circuit web with radially extending flex circuits. The hub 30 is removed prior to affixation of the flex circuit onto the balloon member. As shown in FIG. 2B, each flex circuit 15 has a main portion which carries the electrode 20, a proximal tail portion 35 which extends toward a proximal end of the assembly 13. A proximal tail end (not shown) may be tucked under and affixed by a proximal ring 37 to help fasten the flex circuit 15 on the outer surface of the balloon membrane 28.

As shown in FIG. 4A, each flex circuit has a sheet substrate 40 which supports the electrode 20 and other components including solder patches and thermocouple wires. In accordance with a feature of the present invention, the substrate 40 is constructed of any suitable material with a greater heat resistance than that of the membrane 28 of the balloon member 14. As used herein, heat resistance refers to the ability of a material to withstand high temperatures at which the material melts, degrades or is damaged. For example, a material that begins to melt at a lower temperature has a lesser heat resistance, whereas a material that begins to melt at a higher temperature has a greater heat resistance.

In some embodiments, the substrate is constructed of a thermoset material or a material that can withstand a temperature higher than the melting temperature of the construction material of the balloon membrane 28 by approximately 100 C or more. A suitable material includes polyimide, which is any of a class of polymers with an imido group, that is resistant to high temperatures, wear, radiation, and many chemicals.

In accordance with a feature of the present invention, each flex circuit 15 is preperforated or otherwise formed with apertures 42 by a suitable process prior to affixation to the balloon membrane 28. In other words, apertures 42 are preformed in the substrate 40 of the flex circuit 15 prior to and separately from apertures 44 formed in the balloon membrane 28. A suitable substrate perforation process includes laser cutting, including laser perforation and laser micro perforation. Rather than puncturing or tearing the substrate 40, as is typical with mechanical perforation machines, which tends to weaken the material, laser microperforation burns through the substrate 40, where the result is a cleaner, smaller, rounder, more precise hole. Laser perforating systems operate by using a focused laser pulse to vaporize a very small, well-defined and controlled area or point to form a hole while sealing the hole's edges and strengthening the material around it. With laser micro perforation, hole diameters down to about 5 microns can be achieved. The apertures 42 formed in the substrate 40 via laser perforation have diameters ranging between about 0.001" and 0.010", and preferably are about 0.0035".

Figure 4B:
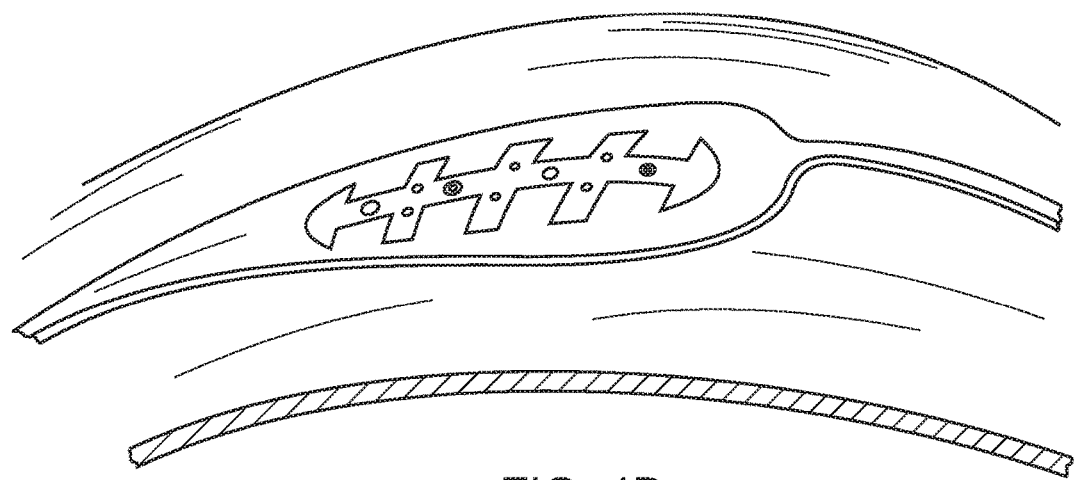
FIG. 4B is a side view of the flex circuit after affixation to the balloon membrane.

After the flex circuits 15 have been perforated with apertures 42, the flex circuits 15 are affixed to the outer surface of the balloon membrane 28 by a suitable adhesive 45, as shown in FIGS. 4A and 4B. The adhesive 45 is allowed to flow between the substrate 40 and the membrane 28 to provide full coverage in order to maximize adhesion. In some embodiments, the balloon member 14 is inflated by the application of positive air pressure into the balloon member 14 during the affixation of the flex circuits 15 to the outer surface of the balloon membrane 28.

Figure 7:
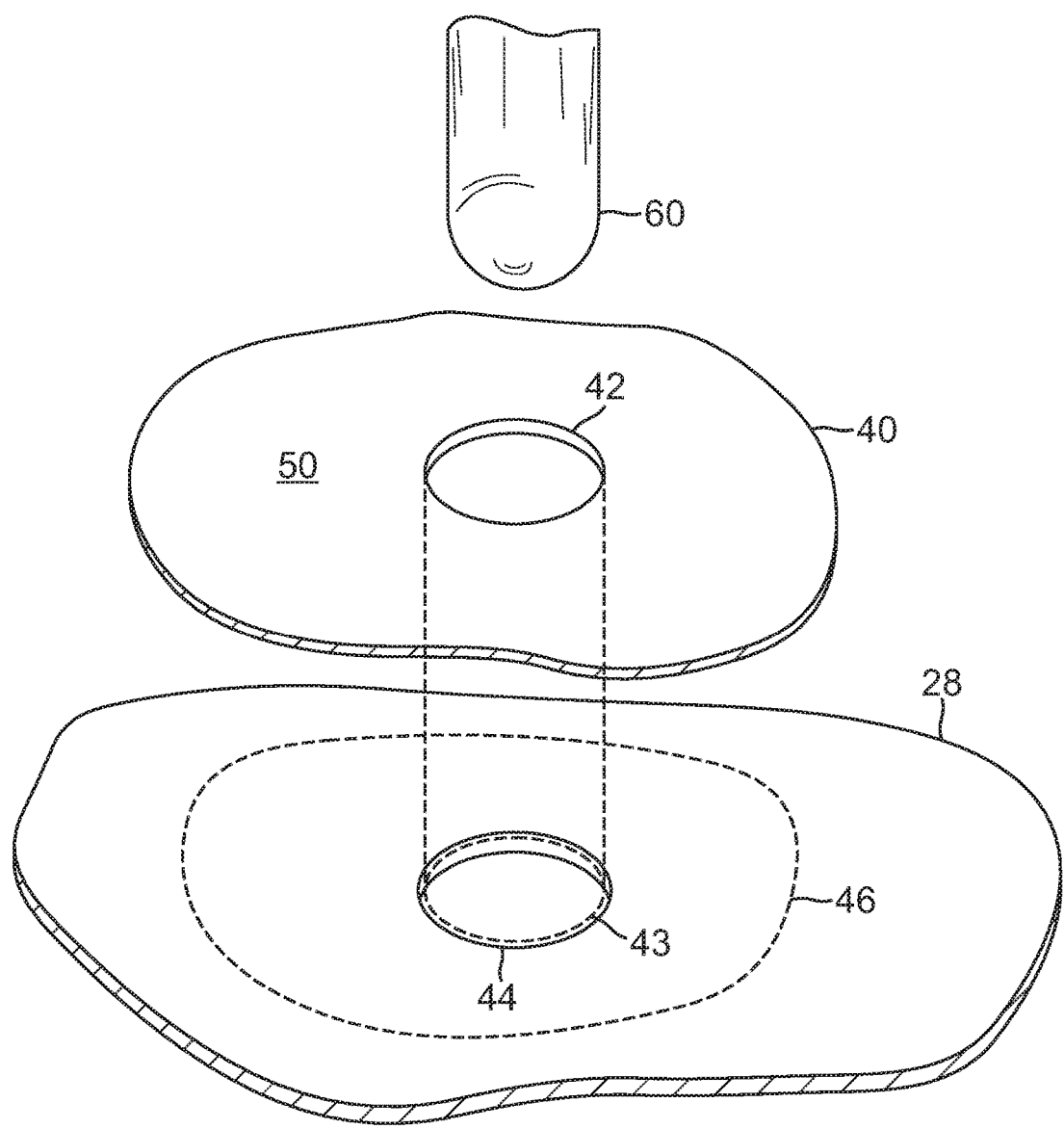
FIG. 7 illustrated the flex circuit and the balloon membrane of FIG. 6, in a detailed exploded view.

For ease in describing the method of the present invention, reference is made to FIG. 7, where a surrounding portion 50 surrounds a pre-formed aperture 42 in the substrate 40. With the substrate 40 affixed to the membrane 28 (both shown in an exploded view in FIG. 7), the pre-formed aperture 42 frames or circumscribes a respective target portion 43 of the membrane at which an aperture 44 can be formed in the membrane 28. The surrounding portion 50 of the substrate 40, when affixed to the membrane 28, masks a surrounding portion 46 of membrane 28 that surrounds the target portion 43.

After the adhesive affixing the membrane 28 and the substrate 40 together has flowed and cured, a heating element 60 is applied to the target portion 43 of the membrane 28 as accessed through the pre-formed aperture 42, with the surrounding portion 50 of the substrate 40 blocking and protecting the masked surrounding portion 46 of the membrane 28 from the applied heat. In this manner, the pre-perforated substrate 40 of the flex circuit 15 when affixed to the balloon membrane 28 serves as a template wherein the pre-formed aperture 42 in the substrate 40 provides a guide by which an aperture 44 in the balloon membrane 28 is formed. The pre-formed apertures 42 in the substrates 40 of the flex circuits 15 advantageously provide an exact and direct guide as to the locations of the apertures 44 in the balloon membrane 28.

In some embodiments, the heat applied may provide or create a temperature of about 200-400 C, but preferably around 250 C. In some embodiment, a source of the heat may be a heating or heated element, for example, a fine tipped soldering iron or a heated fine wire. The heat may also be provided by an energy beam, such as a laser that can provide localized heating (non-excimer) by absorption of the adhesive 45 and the balloon membrane 28 sufficient to melt the adhesive 45 and balloon membrane 28, and not the substrate 40 of the flex circuit 15 masking the membrane 28.

The heat applied creates a temperature sufficient to melt and reflow the balloon membrane 28. Because the substrate 40 has a higher melting temperature, it is unaffected by the heat and it provides a precise orifice size after the material of the balloon membrane 28 reflows away from the heat source. Where the adhesive 45 is reflowable, the heat applied also reflows the adhesive 45 away from the aperture 44.

The reflow is achieved by initial mechanical displacement of the melted materials, but is further helped by surface tension of the melted materials which will form a rim around the underside of the preformed aperture 42.

Accordingly, the reflowing of the adhesive 45 and the balloon membrane 28 via heat applied through the preformed apertures 42 of the flex circuit 15 can result in apertures 44 in the balloon membrane 28 that have at least the same or greater size or diameters than the apertures 42.

Embodiments of the method of manufacturing of the present invention provide a number of benefits and advantages. For example the use of localized heat minimizes or avoids the use of aids in the manufacture or assembly of the balloon member 14 and the flex circuits 15, including the avoidance of using an inner inflated balloon to provide structural support to the balloon member 14. Moreover, there is little difficulty aligning the pre-formed apertures 42 of the substrate 40 with the apertures 44 formed in the balloon membrane 28 because the pre-perforated flex circuit 15 is adhered directly on the balloon membrane 28 after which the apertures 44 are formed, reducing if not eliminating any possibility of misalignment. Furthermore, the use of a heating element in reflowing the balloon membrane 28 and the adhesive 45 provides a physical barrier to any reflowed materials blocking or resealing the newly-formed aperture 44 in the balloon membrane 28. No puncture or drilling is involved so there is no risk of creating debris that may detach from the catheter.

Figure 6:
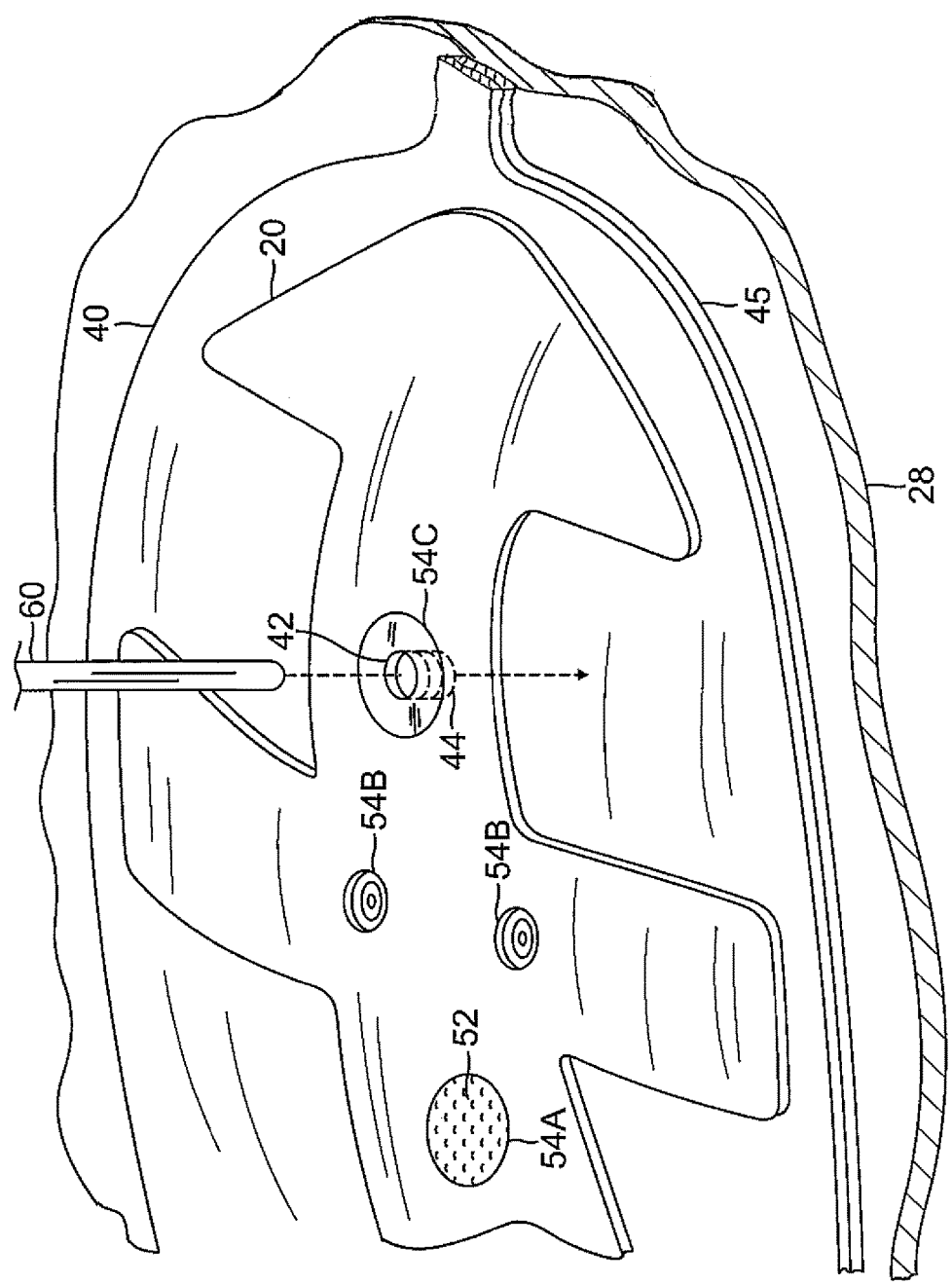
FIG. 6 illustrates the use of pre-formed aperture in a flex circuit in the formation of an aperture in a balloon membrane.

In the embodiment of FIG. 6, the electrode 20 of the flex circuit 15 has one or more voids or cutouts 54 along the spine 22. One cutout 54A is filled with, for example, tungsten-loaded epoxy 52 to serve as markers visible under fluoroscopy. Other smaller cutouts 54B serve as blind vias to provide electrical connections for the electrode 20 from one side (topside) of the substrate 40 to the other side (underside) of the substrate. Another cutout 54C frames a pre-formed aperture 42 in the substrate 40 previously formed by lasercutting before affixation to the balloon membrane 28.

After the flex circuit 15 has been affixed to the balloon membrane 28 by the adhesive 45, and the adhesive has cured, a heating element 60 is inserted through the preformed aperture 42 of the substrate 40 to melt the membrane 28 framed by the preformed aperture 42. The heating element 60 reflows both the adhesive 45 and the membrane 28 and away from the heating element 60 to form the aperture 44 in the membrane 28 that is generally aligned and coaxial with the pre-formed aperture. The pre-formed aperture 42 in the substrate 40 and the subsequent aperture 44 formed in the membrane 28 together provide an irrigation aperture in the inflatable electrode assembly allowing irrigation fluid to pass from inside the balloon member to outside of the inflatable electrode assembly.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale and any feature or combinations of features described in any one embodiment may be incorporated into any other embodiments or combined with any other feature(s) of other embodiments, as desired or needed. Accordingly, the foregoing description should not be read as pertaining only to the precise structures described and illustrated in the accompanying drawings, but rather should be read consistent with and as support to the following claims which are to have their fullest and fair scope.

What is claimed is:

1. A method of constructing an inflatable irrigated electrode assembly for an electrophysiology catheter, the method comprising:
   providing a flex circuit having a substrate with a preformed aperture, the substrate having a higher heat resistance;
   providing an inflated balloon member with a flexible membrane, the membrane having a lower heat resistance;
   affixing the substrate to the membrane with adhesive; and
   applying heat through the pre-formed aperture of the substrate, the heat creating a temperature sufficient to melt a portion of membrane and the adhesive without melting the substrate, the portion of the membrane and the adhesive melted forming an aperture in the membrane and adhesive.

2. The method of claim 1, wherein the substrate is constructed of a thermoset material.

3. The method of claim 1, wherein the substrate is constructed of a material having a higher melting temperature, and the membrane is constructed of a material having a lower melting temperature.

4. The method of claim 1, wherein the substrate is constructed of a material having a higher melting temperature, and the adhesive has a lower melting temperature.

5. The method of claim 1, wherein the membrane is constructed of thermoplastic polyurethane.

6. The method of claim 1, wherein the substrate is constructed of polyimide.

7. The method of claim 1, wherein the applying heat includes inserting a soldering iron into the pre-formed aperture.

8. The method of claim 1, wherein the applying heat includes inserting a hot wire into the pre-formed aperture.

9. The method of claim 1, wherein the applying heat includes directing an energy beam from a laser into the pre-formed aperture to melt the target portion of the membrane and the adhesive.

10. A method of constructing an inflatable electrode assembly configured for irrigation, comprising:
    providing a flex circuit having a substrate with a preformed aperture;
    providing a balloon member with a membrane, the membrane having a first lesser heat resistance;
    affixing the substrate to the membrane with an adhesive wherein a surrounding portion of the substrate around the pre-formed aperture masks a surrounding portion of the membrane so as to expose a target portion of the membrane and the adhesive, the substrate having a greater heat resistance, the adhesive having a second lesser heat resistance; and
    applying heat to the target portion of the membrane through the pre-formed aperture of the substrate, wherein the heat applied, without melting the substrate, melts the target portion of the membrane and the adhesive in forming an aperture in the membrane.

11. The method of claim 10, wherein the heat applied creates a temperature in the membrane that is between the first temperature of the substrate and the melting temperature of the membrane.

12. The method of claim 10, wherein the heat applied creates a temperature in the membrane that is equal or greater than the melting temperature of the membrane.

13. The method of claim 10, wherein the heat applied creates a temperature in the adhesive that is equal or greater than the melting temperature of the adhesive.

14. The method of claim 10, wherein the aperture in the membrane is larger than the pre-formed aperture in the substrate.

15. The method of claim 10, wherein the applying heat includes inserting a soldering iron into the pre-formed aperture.

16. The method of claim 10, wherein the applying heat includes inserting a hot wire into the pre-formed aperture.

17. The method of claim 10, wherein the applying heat includes directing an energy beam from a laser into the pre-formed aperture to melt the target portion of the membrane and the adhesive.

18. The method of claim 10, wherein the affixing the substrate to the membrane includes applying an adhesive between the membrane and the surrounding portion of the substrate, wherein the heat applied to the target portion of the membrane and the adhesive reflows the membrane and the adhesive.

19. The method of claim 10, wherein the membrane is constructed of thermoplastic polyurethane.

20. The method of claim 10, wherein the substrate is constructed of polyimide.

21. A method of constructing an inflatable electrode assembly configured for irrigation, comprising:
   providing a flex circuit having a substrate with a pre-formed aperture, the substrate constructed of a material having a greater heat resistance;
   providing an inflated balloon member with a flexible membrane, the membrane constructed of material having a lesser heat resistance;
   adhering the substrate to the membrane with adhesive, wherein a first surrounding portion of the substrate around the pre-formed aperture frames an exposed target portion of the membrane while masking a second surrounding portion of membrane around the exposed target portion; and
   applying heat to the target portion of the membrane through the pre-formed aperture of the substrate, the heat creating a temperature sufficient to melt the target portion of membrane without melting the first surrounding portion of the substrate.

22. The method of claim 21, wherein the membrane is constructed of thermoplastic polyurethane and the substrate is constructed of polyimide.

* * * * *